US00PP09216P

United States Patent [19]

Klemm

[11] Patent Number: Plant 9,216

[45] Date of Patent: Jul. 25, 1995

[54] GERANIUM PLANT 'KLEIRRO'

[76] Inventor: Siegfried Klemm, Hanfäcker 8,, D 70378 Stuttgart, Germany

[21] Appl. No.: 286,014

[22] Filed: Aug. 4, 1994

[51] Int. Cl.[6] ..... A01H 5/00

[52] U.S. Cl. ..... Plt./87.12

[58] Field of Search ..... Plt. 87.12

*Primary Examiner*—James R. Feyrer

*Attorney, Agent, or Firm*—Arnold, White & Durkee

[57] ABSTRACT

Geranium Kleirro is a new and distinct cultivar of geranium, botanically known as *Pelargonium*×*zonale* Hybriden. It is distinguished from other geranium plants by its rose flower color and compact uniform growing habit.

1 Drawing Sheet

BACKGROUND OF THE NEW PLANT

Kleirro is the product of a controlled breeding program that has the objective of developing new geranium plants with enhanced blue tones to the basically red flowers in combination with other commercially desirable characteristics.

Kleirro originated from the seed parent Klesegmo, named Egmont, and from pollen parent Marix (U.S. Plant Pat. No. 7,257), tradename Courage. Klesegmo has been market tested but is not offered commercially.

The new seedling was discovered in 1987 and selected by the inventor as one flowering plant from among the progeny of the seed parent Klesegmo and the pollen parent Marix. The seed from Klesegmo was obtained after pollination of Klesegmo with Marix. Kleirro differed from each parent in having a distinctly more blue color than either parent. Parent Klesegmo and parent Marix both have bluish pink flowers.

The first act of asexual reproduction of Kleirro was accomplished when vegetative cuttings were taken from the initial selection in a controlled environment in Stuttgart, Germany, by the inventor or technicians working under the supervision of the inventor. Horticultural examination of selected plants demonstrated that the combination of characteristics herein disclosed for Kleirro are firmly fixed and are retained through successive generations of asexual reproduction.

Kleirro has not been observed under all possible environmental conditions. The phenotype may vary significantly with variations in environment such as temperature, light intensity, and day length. The following observations, measurements, and comparisons describe plants grown in Stuttgart, Germany, under conditions that approximate those used in commercial practice. Similar characteristics are found when the plant is grown under controlled environmental conditions in Italy, The Netherlands and Teneriffe.

Of the many varieties of the same species of geranium plant known to the inventor, Kleirro by comparison has good precocity and is earlier blooming in warmer climates with excellent floral richness particularly in hot climates. The growth is uniform and compact with very good self-branching, transportability of marketable plants is good because of non-shattering characteristics of the flowers. Weather resistance of the flowers and foliage is good although the leaves are not very dark. The leaves are resistant to cold and heat without rotting or turning yellow or red. Flowers appear abundantly and continuously without a break during the whole summer. The plant performs well in a garden in all climates where geraniums can be grown. Propagation is readily accomplished and rooting time is relatively short. Cutting protection is good as is transportability of rooted or unrooted cuttings.

Flower color is attractive because of brightness and clarity. The filling and flower shape is defined by the broad petals with entire margins. The umbels stand on vertical stems and are nicely postured on the plant. The green foliage stands in good contrast to the cool and frosty flower color giving the overall appearance of flowering plants of this new cultivar high market appeal.

The new cultivar Kleirro most closely resembles geranium PAC Laura and SelCourage; however, both of these geraniums have distinctly different flower color from the new cultivar.

DESCRIPTION OF THE PHOTOGRAPH

The accompanying color photograph of Kleirro illustrates typical inflorescence and leaf characteristics of the new plant. The plant was photographed using professional photographic techniques. The view is taken against a purple background that illustrates flower color closest to the color values in accordance with The Royal Horticultural Society Colour Chart. The purple background highlights the rich, bluish rose color of the flowers.

DESCRIPTION OF THE PLANT

The following description uses color references from The Royal Horticultural Society Colour Chart. The color values were determined under prevailing conditions of natural daylight in a greenhouse environment during the month of March in Stuttgart, Germany.

The following traits have been repeatedly observed and are determined to be basic characteristics of Kleirro that in combination distinguish this geranium as a new and distinct cultivar. There characteristics include a semi-double blue rose flower color with a white center, early blooming, floriferous, and a uniform and compact growing habit.

Classification:

*Botanical.*—*Pelargonium*×*zonale* Hybriden.

*Commercial.*—Kleirro, Zonale Geranium.

The Plant

Form (Observed from above): Well-branched bush, round shape.

Height: Medium, reaches 180 mm when marketable in April; reaches up to 220 mm by the end of the season.

Internode length: Approximately 10 mm.

Growth rate: Medium.

Rooted cutting to flowering stage: 94 days under commercial greenhouse "cold conditions".

Pinching to induce branching: Not required, this plant readily breaks from the basal nodes of the initial rooted cutting after planting.

Stem length: 140–150 mm indoor; 120–140 mm outdoor in summer.

Precocity: Early.

Length of leaf stem: 50–60 mm.

Branching character: Very good.

Number of stems per stalk: 2–3.

Number of stalks per plant: 5–7.

Growth habit: Upright, medium vigorous.

Foliage:

*Quantity.*—Abundant, rapidly covers the pot.

*Leaf size.*—4.5–6.0 cm length; 8–10 cm width.

Leaf shape.—Half round.

*Margin type.*—Bicrenated.

*Texture.*—Smooth.

*Color.*—Upperside. — 146B. Underside. — 147B. Zonation. — Inconspicuous to none.

Inflorescence

Umbel:

*Shape.*—Round.

*Blooming habit.*—Continuous.

*Pinching.*—Not required to maintain continuous bloom (optional to improve appearance).

*Blooms.*—Profuse.

*Blooming period.*—April to October.

*Time of blooming.*—Early (has a tendency to give fewer blooms in the Fall when weather is cold and rainy).

*Size of cluster.*—Medium (when more than 20 florets are opened).

*Length of pedicel.*—2.3 cm to 2.6 cm, depending on light and temperature.

*Color of pedicel.*—Brown when flowers open, green while still in bud.

*Diameter.*—90 mm.

*Depth.*—80 mm.

*Shape of umbel.*—Round.

*Number of florets per cluster.*—40–50.

Petalage:

*Number of petals.*—7.

Flower size.—55 mm.

*Fullness.*—Semidouble.

*Shape.*—Cup-shaped on first opening flatter with maturity.

*Arrangement.*—Imbricated.

Petal:

*Form.*—Broad.

*Margin type.*—Entire.

*Petal persistence on stem.*—5 days if not pollinated.

*Texture.*—Soft.

*Appearance.*—Velvety.

*Color.*—Outer petal: Body. — RHS 71D. Reverse side. — RHS 67B. Inside petal: Body. — 67B. Reverse side. — RHS 67B.

*Basal part.*—RHS 155D (white); the claw portion of the petals is near white and suffuses progressively to the predominant color of the petal with increased distance from the petal attachment point. The coloration of the veins is darker than the white basal part of the petals and approaches the predominant color of the top surface of the petals which is RHS 67B.

*Length.*—2.5–2.7 cm.

*Width.*—2.0–2.3 cm.

Petaloids:

*No.*—1–5.

*Size.*—1.0–1.8 cm in length, 0.5–0.9 cm wide.

*Color.*—67C.

Peduncle (flower stem):

*Pedicel posture.*—Ascending with the opening of the flower.

*Pedicel thickness.*—Similar to that of other members of the species and sufficiently strong to position flowers as they open.

*Pedicel arrangement.*—Radiating from the apex of the peduncle is typical of most members of the species.

*Discoloration after full bloom.*—Very little, occasionally observed outdoors in summer.

*Effect of hot or wet weather.*—Non observed.

*Persistence.*—At full maturity, no black rot observed.

*Disease resistance.*—Somewhat resistant to botrytis.

*Fragrance.*—None.

Lasting quality:

*Plant.*—More than 17 days.

*Cut flower.*—5 days.

Concerning lasting quality, flowers were observed to determine how long appearance was maintained without picking off old flowers. Also observed was the time required from the day when the first flower opens to the day when the last flower opens. This depends on the number of florets found in one cluster and with geraniums generally may vary from 20 to 70 or more. Characteristics described are based on how long the flowering clusters maintained their appearance without picking off the old flowers.

Bud (measured when petals show original flower color):

*Size.*—Thick and short.

*Diameter.*—9 mm.

*Depth or length.*—10 mm.

*Form or shape.*—Nearly round and globular.

*Rate of opening.*—Average compared with other geraniums having semi-double flowers (single flowers open more quickly).

*Petal color.*—When septals first divide. — Light purple (lilac). When petals being to unfurl. — Light purple (lilac.)

*Sepals.*—Shape. — Long and pointed. Number. — 5 (sepals splay to a reflexed position). Color: Inside. — 144B. Outside. — 143B.

*Number of buds and flowering clusters.*—Young plants. — 2 buds, 1 cluster (April when plants start to flower and are marketable).

*Number of clusters between date of marketablility in middle of May.*—About 5 matured clusters.

*Number of clusters from the middle of May to the end of September.*—Approximately 90 clusters (more during hot, summer weather).

Reproductive Organs:

*Perfect.*—Contains both pistils and stamens.

*Stamens.*—Number. — 5-6 arranged around the ovaries. Anthers: Size. — 2.1 mm. Color. — Red. Filaments (threads): Length. — 7 mm. Color. — Light pink. Pollen: Color. — Orange.

*Pistils.*—Number. — 1 with 5-6 branched stigma

*Styles.*—Length.— 11 mm. Color. — Green and dark red.

*Stigmas.*—Color. — Dark red.

Fruit:

*Fertile.*—Yes.

*Color.*—Green later becoming sand colored.

*Length of seed.*-3.4—4.5 mm.

*Color of seed.*—Brown.

What is claimed is:

1. A new and distinct geranium cultivar, substantially as herein described and shown, characterized by its bluish rose flower color with a white center, floriferous characteristics and uniform and compact growing habit.

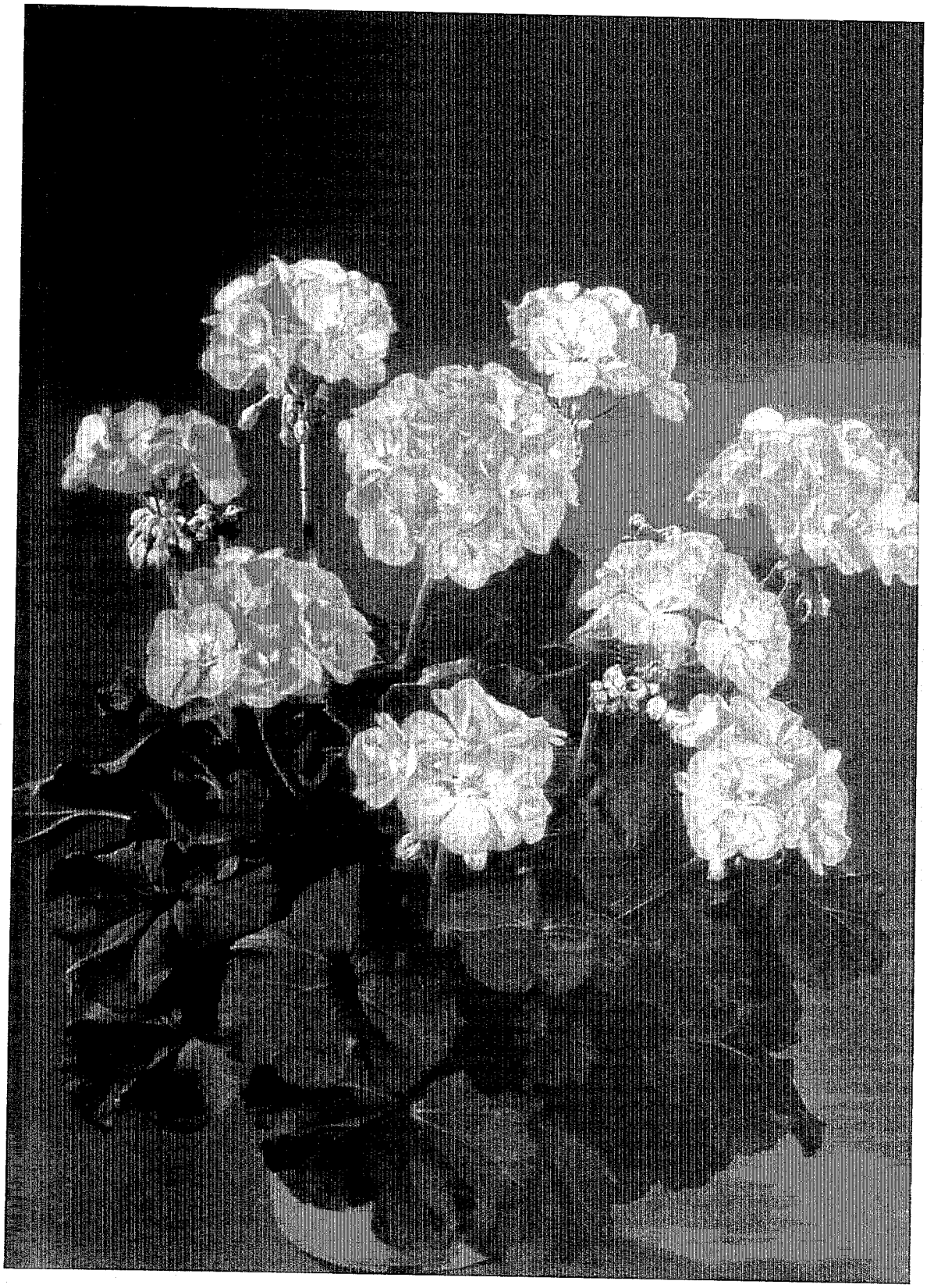

* * * * *